United States Patent
Knopp et al.

(10) Patent No.: US 6,646,152 B1
(45) Date of Patent: Nov. 11, 2003

(54) METHOD OF PRODUCING 2-HYDROXYCARBOXYLIC ACID ESTERS

(75) Inventors: Monika Knopp, Ludwigshafen (DE); Rolf Jansen, Mannheim (DE)

(73) Assignee: Abbott GmbH & Co. KG (DE)

( * ) Notice: Subject to any disclaimer, the term of this patent is extended or adjusted under 35 U.S.C. 154(b) by 29 days.

(21) Appl. No.: 10/070,759

(22) PCT Filed: Sep. 13, 2000

(86) PCT No.: PCT/EP00/08952

§ 371 (c)(1), (2), (4) Date: Mar. 12, 2002

(87) PCT Pub. No.: WO01/19774

PCT Pub. Date: Mar. 22, 2001

(30) Foreign Application Priority Data

Sep. 14, 1999 (DE) .......................... 199 44 049

(51) Int. Cl.⁷ ............................... C07C 69/76

(52) U.S. Cl. .................. 560/57; 560/126; 560/145; 560/179

(58) Field of Search .................. 560/57, 126, 145, 560/179

(56) References Cited

U.S. PATENT DOCUMENTS 3,024,287 A * 3/1962 Kennedy
4,069,260 A * 1/1978 Watson

OTHER PUBLICATIONS

Boireau. Tetrahedron, vol.36, pp. 3061–3070 (1980).*
J Am. Chem. Soc., vol. 100, pp. 3950–3951 (1978).*

* cited by examiner

Primary Examiner—Michael L. Shippen
(74) Attorney, Agent, or Firm—Keil & Weinkauf

(57) ABSTRACT

A process for preparing 2-hydroxycarboxylic esters having a quaternary β-carbon atom by reaction of glycidyl esters with an organoaluminum reagent is described.

7 Claims, No Drawings

METHOD OF PRODUCING 2-HYDROXYCARBOXYLIC ACID ESTERS

The present invention relates to a process for preparing 2-hydroxycarboxylic esters having a quaternary β-carbon atom.

Endothelin receptor antagonists are novel active compounds for the treatment of various cardiovascular disorders. WO 97/38981 describes various endothelin receptor antagonists, for example (S)-3,3-diphenyl-2-(4,6-dimethylpyrimid-2-yloxy)butyric acid. According to the description in WO 97/38981, this compound is obtained from (S)-2-hydroxy-3,3-diphenylbutyric acid by reaction with 4,6-dimethylpyrimidin-3-yl sulfone. 2-Hydroxy-3,3-diphenyl-butyric acid for its part is obtained by reducing 2,2-diphenylpropionitrile to the aldehyde, which is converted into the cyanohydrin which is then subjected to acid hydrolysis. However, this process has a number of disadvantages. The cyanohydrin synthesis involves the handling of hydrogen cyanide, which is objectionable for safety and health reasons. Furthermore, 2,2-diphenylpropionitrile is a comparatively expensive starting material, and the overall yield obtained by this route is unsatisfactory.

It is an object of the present invention to provide an alternative process for preparing 2-hydroxycarboxylic acids having a quaternary β-carbon atom, and/or esters thereof.

Fukumasa et al., THL 32 (1991), 1059–1062, describe the reaction of monosubstituted epoxides with trimethylaluminum.

Danishewsky, S. et al., J. Org. Chem. 41 (1976), 1669–1671, describe the use of functionalized alanes for converting epoxides into trans-fused γ-lactones.

Kuran, W. et al., J. Organomet. Chem 73 (1974), 187–193, describe the reaction of methylaluminum compounds with propylene oxide.

Visnick, M. et al. Synthesis 1983, 284–287, describe the addition of t-butoxycarbonylmethyldiethylalane to 1-alkylidene-2,3-epoxy-3-methylcyclohexanes.

Pfaltz, A. et al., Angew. Chem. Int. Ed. Engl. 21 (1982), 71, report the regioselective ring-opening of α- and β-alkoxyepoxides with trimethylaluminum in the presence of catalytic amounts of butyllithium or lithium methoxide.

Alexakis, A. et al., Tetrahedron 45 (1989), 6197–6202, describe the boron-trifluoride-supported ring-opening of epoxides by lithium alkenyl aluminate reagents. The epoxides used were cyclohexene oxide and n-butyl epoxide.

In a general manner, Gorzynski-Smith, J., Synthesis 1984, 634, refers to the possibility of reacting epoxides with organoaluminum compounds. Simple trialkyl alanes are said to be of limited utility, since the reaction is accompanied by undesirable side-reactions, such as the reduction of the epoxide.

Miyashita, M. et al., J. Org. Chem. 56 (1991), 6483–6485, describe the stereospecific methylation of γ,δ-epoxy acrylates by trimethylaluminum in the presence of water. Miyashita, M. et al., Tetrahedron Asym. 4 (1993), 157.3–1578, describe the use of the epoxide ring-opening with trimethylaluminum in the presence of water in the synthesis of (−)-serricornin. Miyashita, M. et al., Chem. Soc., Chem. Commun. 9 (1996), 1027–1028, describe the use of the epoxide ring-opening with trimethylaluminum in the presence of water in the synthesis of the ansa chain segment of streptovaricin U.

Poon, T. et al., Synthesis 1998, 832, disclose the following reaction:

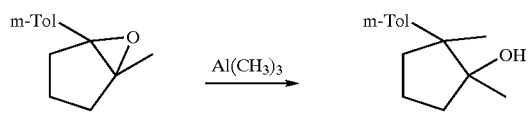

The above literature references do not disclose any reactions in which the epoxide ring carries an ester group.

Neukom, C. et al., J. Am. Chem. Soc. 108 (1986), 5559–5568, describe the reaction of ethyl trans-2,3-epoxybutyrate with diethylpropynylalane. Bartlett, A. et al., J. Org. Chem. 47 (1982), 3941–3945, describe the reaction of ethyl trans-2,3-epoxybutanoate with diethyltrimethylsilylethylalane. The conversion into the α-hydroxy esters with a tertiary β-carbon atom succeeds with only moderate yields.

We have found that the object of the invention is achieved by a process for preparing 2-hydroxycarboxylic esters of the formula I

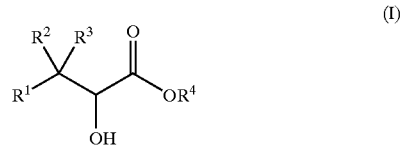

in which $R^1$ and $R^2$ independently of one another are $C_1$–$C_{20}$-alkyl, $C_3$–$C_8$-cycloalkyl, $C_2$–$C_{20}$-alkenyl, $C_2$–$C_{20}$-alkynyl, $C_6$–$C_{10}$-aryl, $C_7$–$C_{14}$-aralkyl or $C_7$–$C_{20}$-alkylaryl, or $R^1$ and $R^2$ together with the carbon atom to which they are attached form a 5- to 8-membered ring;

$R^3$ is $C_1$–$C_{20}$-alkyl, $C_2$–$C_{20}$-alkenyl or $C_2$–$C_{20}$-alkynyl;

$R^4$ is $C_1$–$C_{20}$-alkyl, $C_3$–$C_8$-cycloalkyl, $C_2$–$C_{20}$-alkenyl, $C_2$–$C_{20}$-alkynyl, $C_6$–$C_{10}$-aryl, $C_7$–$C_{14}$-aralkyl or $C_7$–$C_{20}$-alkylaryl;

which comprises reacting a glycidyl ester of the formula II

in which $R^1$, $R^2$ and $R^4$ are as defined above with an organoaluminum reagent of the formula III

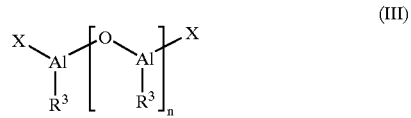

in which $R^3$ is as defined above, X in each case independently have the meanings given for $R^3$ or are halogen or $C_1$–$C_4$-alkoxy and n is from 0 to 10.

Suitable $C_1$–$C_{20}$-alkyl groups are straight-chain and branched alkyl groups, for example $C_1$–$C_8$-alkyl, such as methyl, ethyl, propyl, n-butyl, isobutyl, t-butyl, pentyl.

Suitable $C_3$–$C_8$-cycloalkyl groups are cyclopropyl, cyclobutyl, cyclopentyl or cyclohexyl.

Suitable $C_2$–$C_{20}$-alkenyl groups are, preferably, $C_1$–$C_8$-alkenyl, such as vinyl, allyl, 1-hexenyl.

Suitable $C_2$–$C_{20}$-alkynyl groups are, preferably, $C_1$–$C_8$-alkynyl, for example ethynyl or propynyl.

Suitable $C_6$–$C_{10}$-aryl groups are, in particular, phenyl or naphthyl.

Suitable $C_7$–$C_{14}$-aralkyl groups are, for example, benzyl or phenethyl.

Suitable $C_7$–$C_{20}$-alkylaryl groups are, for example, 2-, 3-, 4-methylphenyl, 2,3-, 2,4-, 2,5-, 2,6-, 3,4-, 3,5-dimethylphenyl or 2,4,6-trimethylphenyl.

Preferably, at least one of the radicals $R^1$ and $R^2$ is aryl, aralkyl or alkylaryl, cycloalkyl or branched alkyl, in particular alkyl having a branch in the 1- or 2-position, such as isopropyl, t-butyl, isobutyl.

Particularly preferably, $R^1$ and $R^2$ are both phenyl.

$R^1$, $R^2$ and $R^3$ may carry 1, 2, 3, 4 or 5 substituents which do not negatively affect the reaction according to the invention, such as, for example, $C_1$–$C_6$-alkyl, $C_1$–$C_6$-alkoxy, di($C_1$–$C_6$-alkyl)amino, nitro, ester (for example $CO_2R^5$, where $R^5$ may have the meanings given for $R^4$), amide, sulfonamide, silyl or nitrile groups.

The glycidyl esters of the formula II can be obtained, for example, by Darzens glycidyl ester synthesis from corresponding ketones, by reaction with chloroacetic esters and base. Furthermore, they can be obtained, for example, by epoxidation of suitably substituted cinnamic esters. They may have the (S) or (R) configuration at the α-carbon and may be present as pure or enriched enantiomers or as racemate. If $R^1 \neq R^2$, it is also possible for both configurations to be present at the β-carbon.

$R^3$ is preferably methyl, ethyl, n-butyl, particularly preferably methyl. $R^3$ may furthermore be, for example, AlkOCO—$CH_2$—, AlkO—C≡C—, Alk-C≡C—, Alk-CH=CH—, Alk-CH=CH—$CH_2$—, in which Alk is $C_1$–$C_4$-alkyl.

In the formula III, X has the meanings given for $R^3$, in particular $C_1$–$C_4$-alkyl; halogen, such as fluorine, chlorine or bromine; or $C_1$–$C_4$-alkoxy.

The index n is preferably 0. Particularly preferred organoaluminum reagents are trimethylaluminum, triethylaluminum and tributylaluminum, trimethylaluminum being most preferred. Other suitable reagents are, for example, AlkOCOCH$_2$Al(C$_2$H$_5$)$_2$, Alk-CH=CH—Al(C$_2$H$_5$)$_2$.

Organoaluminum reagents in which n≠0 are known under the term alumoxanes, and they can be obtained by controlled reaction of aluminum organyls with water (cf., for example, DE-A-37 31 665).

The reaction according to the invention of the glycidyl ester of the formula II with the organoaluminum reagent of the formula III is preferably carried out at a temperature of less than 20° C., in particular at from −10 to +10° C.

The reaction according to the invention is advantageously carried out in a nonpolar solvent, preferably an aliphatic or aromatic hydrocarbon or a mixture of aliphatic and/or aromatic hydrocarbons, such as hexane, heptane, cyclohexane, benzene, toluene or xylene.

The reaction time is generally from 0.5 to 2 h. After the reaction has ended, the reaction mixture is generally worked up acidic-aqueous; the 2-hydroxycarboxylic ester of the formula I is isolated by customary methods. If desired, the ester can be converted into the parent acid.

In the reaction according to the invention, the organoaluminum reagent of the formula III is preferably employed in excess. Particularly preferably, the molar ratio of the organoaluminum reagent of the formula III to the glycidyl ester of the formula II is in the range from 1.3 to 1.5. Higher excesses of organoaluminum reagent of the formula III may lead to a worsening of the regioselectivity.

The reaction according to the invention can be carried out both by adding the organoaluminum reagent to a solution of the glycidyl ester, preferably in a nonpolar solvent, or by adding the glycidyl ester, preferably as a solution in a nonpolar solvent, to a solution of the organoaluminum reagent. A reaction procedure where a solution of the glycidyl ester in toluene is added to a solution of the organoaluminum reagent in heptane or cyclohexane has been found to be particularly useful.

In the reaction according to the invention, the radical $R^3$ is introduced substantially regioselectively into the β-position to the ester group. The regioselectivity is generally more than 80%, preferably more than 90%. The reaction takes place predominantly with retention of the configuration at the carbon which carries the ester group. If glycidyl esters having a defined stereochemistry are used, it is therefore possible to obtain essentially pure enantiomers.

Surprisingly, the reaction of the glycidyl ester with the organoaluminum reagent generally succeeds without addition of further activating reagents, such as tertiary amines, lithium alkoxides or lithium alkyls, even if the starting material used is a sterically hindered glycidyl esters.

Surprisingly, in the reaction of the glycidyl ester with the alkylaluminum reagent, there are furthermore no side-reactions, such as, for example, elimination to give α,β-unsaturated esters, or pinacol rearrangements, to be observed. This is particularly surprising, since trialkylaluminum, for example, is known to catalyze pinacol rearrangements.

The invention is now illustrated in more detail by the examples below.

EXAMPLE 1

Epoxide Opening in Heptane at −10° C. Using 1.3 Equivalents of Trimethylaluminum (TMA)

190 g (747 mmol) of methyl 2,3-epoxy-3,3-diphenylpropionate were dissolved in 80 ml of toluene and added to 920 ml of heptane. At −10° C., 486 ml (971 mmol) of 2M trimethylaluminum solution in toluene were added. After the addition had ended, a slightly yellow suspension was present. Stirring was continued for 30 minutes. At 5–10° C., the reaction mixture was added dropwise with stirring to a mixture of 975 ml of ice-water and 150 ml of concentrated sulfuric acid. The reaction mixture was heated at 40–45° C. The organic phase was separated off and washed once with 250 ml of water. The organic phase was concentrated, giving the product in the form of a yellow solid.

Yield: 194 g (96%) Regioselectivity (methyl group in β-/α-position; determined by HPLC): 97:3

EXAMPLE 2

Epoxide Opening in Heptane at −10° C. Using 1.3 Equivalents of TMA in Inverse Operation 97.5 ml (195 mmol) of 2M trimethylaluminum solution in toluene were initially charged in 210 ml of heptane and, at −10° C., admixed with 38.1 g (150 mmol) of methyl 2,3-epoxy-3,3-diphenyl-propionate. The reaction mixture was stirred for another 30 minutes and then, at 5–10° C., added dropwise with stirring to a mixture of 195 g of ice-water and 30 ml of concentrated sulfuric acid. The reactor was washed with 200 ml of toluene. The reaction mixture was heated to 40–45° C. The organic phase was separated off and the aqueous phase was reextracted once with 200 ml of toluene. The combined organic phases were concentrated, giving the product in the form of a yellow solid.

Yield: 33.3 g (82%) Regioselectivity: 98:2

EXAMPLE 3

Epoxide Opening in Cyclohexane at 5° C. Using 1.3 Equivalents of TMA (6.25% Strength Solution)

5.0 g (19.7 mmol) of methyl 2,3-epoxy-3,3-diphenylpropionate were suspended in 80 ml of cyclohexane. At 10 to 15° C., 15 ml (30 mmol) of 2M trimethylaluminum solution in toluene were added. After the addition had ended, a clear yellow solution was present. Stirring was continued for 30 minutes. At 5–10° C., the reaction mixture was added dropwise with stirring to 250 ml of 1M HCl solution. A further 60 ml of toluene were added. The organic phase was separated off and the aqueous phase was reextracted once with toluene. The combined organic phases were concentrated, giving the product in the form of a yellow solid.

Yield: 5.33 g (100%) Regioselectivity: 97:3

EXAMPLE 4

Example 3 was repeated, but the reaction was carried out in cyclohexane at 10° C., using 1.3 equivalents of TMA (20% strength solution).

Yield: 96% Regioselectivity: 90:10

EXAMPLE 5

Example 3 was repeated, but the reaction was carried out in toluene at −10° C., using 1.3 equivalents of TMA.

Yield: 82% Regioselectivity 91:9

EXAMPLE 6

Example 3 was repeated, but the reaction was carried out in toluene at 0° C., using 1.5 equivalents of TMA.

Yield: 100% Regioselectivity: 90:10

EXAMPLE 7

Example 3 was repeated, but the reaction was carried out in toluene at 10° C., using 1.5 equivalents of TMA.

Yield: 87% Regioselectivity: 78:22

EXAMPLE 8

Example 3 was repeated, but the reaction was carried out in toluene at 0° C., using 2 equivalents of TMA.

Yield: 87% Regioselectivity: 86:14

We claim:

1. A process for preparing 2-hydroxycarboxylic esters of the formula I

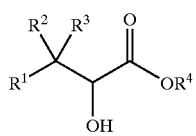

(I)

in which

R$^1$ and R$^2$ independently of one another are $C_1$–$C_{20}$-alkyl, $C_3$–$C_8$-cycloalkyl, $C_2$–$C_{20}$-alkenyl, $C_2$–$C_{20}$-alkynyl, $C_6$–$C_{10}$-aryl, $C_7$–$C_{14}$-aralkyl or $C_7$–$C_{20}$-alkylaryl, or R$^1$ and R$^2$ together with the carbon atom to which they are attached form a 5- to 8-membered ring;

R$^3$ is $C_1$–$C_{20}$-alkyl, $C_2$–$C_{20}$-alkenyl or $C_2$–$C_{20}$-alkynyl;

R$^4$ is $C_1$–$C_{20}$-alkyl, $C_3$–$C_8$-cycloalkyl, $C_2$–$C_{20}$-alkenyl, $C_2$–$C_{20}$-alkynyl, $C_6$–$C_{10}$-aryl, $C_7$–$C_{14}$-aralkyl or $C_7$–$C_{20}$-alkylaryl;

which comprises reacting a glycidyl ester of the formula II

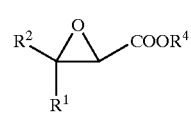

(II)

in which R$^1$, R$^2$ and R$^4$ are as defined above with an organoaluminum reagent of the formula III

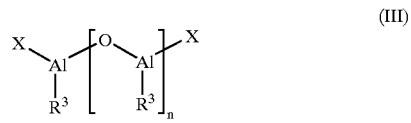

(III)

in which R$^3$ is as defined above, X in each case independently have the meanings given for R$^3$ or are halogen or $C_1$–$C_4$-alkoxy and n is from 0 to 10.

2. A process as claimed in claim 1, wherein the organoaluminum reagent is trimethyl aluminum.

3. A process as claimed in claim 1, wherein R$^1$ and R$^2$ are both phenyl.

4. A process as claimed in claim 1, wherein the reaction of the glycidyl ester of the formula II with the organoaluminum reagent of the formula III is carried out at from −10 to +10° C.

5. A process as claimed in claim 1, wherein the reaction of the glycidyl ester of the formula II with the organoaluminum reagent of the formula III is carried out in a solvent selected from the groups consisting of aliphatic and aromatic hydrocarbons.

6. A process as claimed in claim 1, wherein the molar ratio of the organoaluminum reagent of the formula III to the glycidyl ester of the formula II is in the range from 1.3 to 1.5.

7. A process as claimed in claim 1, wherein the glycidyl ester of the formula II is added to a solution of the organoaluminum reagent of the formula III.

\* \* \* \* \*